(12) United States Patent
Barbour et al.

(10) Patent No.: US 7,142,304 B1
(45) Date of Patent: Nov. 28, 2006

(54) METHOD AND SYSTEM FOR ENHANCED IMAGING OF A SCATTERING MEDIUM

(75) Inventors: Randall L. Barbour, Glen Head, NY (US); Yaling Pei, Morris Plains, NJ (US)

(73) Assignee: The Research Foundation of State University of New York, Albany, NY (US)

( * ) Notice: Subject to any disclaimer, the term of this patent is extended or adjusted under 35 U.S.C. 154(b) by 482 days.

(21) Appl. No.: 10/088,185

(22) PCT Filed: Sep. 14, 2000

(86) PCT No.: PCT/US00/25157

§ 371 (c)(1),
(2), (4) Date: Mar. 14, 2002

(87) PCT Pub. No.: WO01/20307

PCT Pub. Date: Mar. 22, 2001

Related U.S. Application Data

(60) Provisional application No. 60/153,769, filed on Sep. 14, 1999.

(51) Int. Cl.
*G01N 21/00* (2006.01)

(52) U.S. Cl. .................................. 356/432; 356/436

(58) Field of Classification Search ........ 356/432–436; 250/227.27; 600/473, 476, 342
See application file for complete search history.

(56) References Cited

U.S. PATENT DOCUMENTS

| | | | | |
|---|---|---|---|---|
| 5,659,397 A | * | 8/1997 | Miller et al. | 356/446 |
| 5,920,390 A | * | 7/1999 | Farahi et al. | 356/477 |
| 5,994,690 A | | 11/1999 | Kulkarni et al. | |
| 6,075,610 A | * | 6/2000 | Ueda et al. | 356/432 |
| 6,542,772 B1 | * | 4/2003 | Chance | 600/473 |
| 6,640,133 B1 | * | 10/2003 | Yamashita et al. | 600/476 |
| 6,694,159 B1 | * | 2/2004 | Hall et al. | 600/310 |

* cited by examiner

*Primary Examiner*—Michael P. Stafira
(74) *Attorney, Agent, or Firm*—Scully, Scott, Murphy & Presser, P.C.

(57) ABSTRACT

The present invention recognizes that contrary to intuitive expectations, sensitivity and resolution of the data for image reconstruction can be increased by decreasing the absorption or scattering mean free path length of the imaging source energy. Methods are disclosed in this respect for enhancing sensitivity and resolution in the imaging of scattering target media (116). In one method, source energy wavelength is selected to optimize scattering and absorption of the energy while maintaining measurable and acceptable detector signals (112). In another aspect of the invention, the scattering target medium (116) is radially compressed and the imaging source wavelength is then adjusted in conjunction with the compression to improve sensitivity and resolution.

21 Claims, 16 Drawing Sheets

METHOD AND SYSTEM FOR ENHANCED IMAGING OF A SCATTERING MEDIUM

This application claims the benefit under 35 U.S.C. §120 of prior U.S. Provisional Patent Application Ser. No. 60/153,769 filed Sep. 14, 1999, entitled TOMOGRAPHY IN A SCATTERING MEDIUM.

This invention was made with U.S. Government support under contract number RO1-CA66184, awarded by the National Institutes of Health. The U.S. Government has certain rights in the invention.

FIELD OF THE INVENTION

The invention relates to the field of imaging in a scattering medium, and more particularly to optimization of source parameters to enhance the resolution and sensitivity of measured data and the reconstructed image of the medium.

BACKGROUND OF THE INVENTION

Imaging in a scattering medium relates generally to the methods and techniques of generating an image of the internal properties of a scattering medium on the basis of detected scattered energy.

Many systems and techniques have been developed for imaging of scattering media. A typical system for imaging based on scattered energy detection includes a source for directing energy into a target medium and at least one detector, at one or more locations with respect to the source, for measuring the scattered energy exiting the target medium. From these measurements of energy exiting the target medium, it is possible to reconstruct images that represent the scattering and absorption properties of the target. The absorption and scattering properties of the medium are a function of the medium itself, and of the wavelength and type of energy employed as an imaging source.

Exemplary methods and systems for imaging of a scattering media are disclosed in Barbour et al., U.S. Pat. No. 5,137,355, entitled "Method of Imaging a Random Medium," (hereinafter the "Barbour '355 patent"), Barbour, U.S. Pat. No. 6,081,322, entitled "NIR Clinical Opti-Scan System," (hereinafter the "Barbour '322 patent"), U.S. Pat. No. 6,795,195, entitled "SYSTEM AND METHOD FOR TOMOGRAPHIC IMAGING OF DYNAMIC PROPERTIES OF A SCATTERING MEDIUM" by inventors R. L. Barbour and C. H. Schmitz (hereinafter the "Barbour '195 patent"), U.S. Pat. No. 6,937,884, entitled "METHOD AND SYSTEM FOR IMAGING THE DYNAMICS OF A SCATTERING MEDIUM" by inventor R. Barbour and is hereby incorporated by reference (hereinafter the "Barbour '884 patent").

Imaging techniques based on these known systems and techniques measure the internal absorption and scattering properties of a medium using sources whose propagating energy is highly scattered. This permits the use of wavelengths and types of energy not suitable for projection imaging techniques. Thus these techniques have great potential for detecting properties of media that are not accessible to energy sources used for projection imaging techniques (e.g., x-rays).

As can readily be appreciated, there are many instances where these techniques are highly desirable. For example, one flourishing application is in the field of optical tomography. Optical tomography typically uses near infrared radiation (i.e., electromagnetic radiation with wavelengths in the range of ~750—~1200 nanometers) as an energy source. Near infrared radiation is highly scattered in human tissue and is therefore an unsuitable source for practical projection imaging in the human body. However, these properties make near infrared radiation a superior imaging source for scattering imaging techniques. The ability to use near infrared radiation as an imaging source is of particular interest in the human body because the strength of the interactions between the radiation and tissue are exceptionally responsive to blood oxygenation levels and blood volumes. These attributes permit imaging of the vasculature, and thus provide great potential for detecting cardiovascular disease, tumors and other disease states.

Of central importance to these and other imaging methods is an appreciation of the limits of sensitivity and achievable resolution of the reconstructed image. In the case of simple projection imaging, the properties of the point-spread function largely determine the sensitivity and resolution limits. In model-based techniques for imaging of scattering media, sensitivity and resolution are strongly influenced by a complex relationship between a host of parameters associated with the target properties (i.e., target domain), conditions and quality of collected data (i.e., measurement domain) and stability and accuracy of numerical methods used for image recovery (i.e., analysis domain). However, sensitivity and resolution are ultimately limited by the quality of the collected data. Known methods and systems for imaging of scattering media provide images having relatively low resolution and sensitivity.

For the foregoing reasons, there is an ongoing need for methods of improving the quality of the data collected from a scattering medium in a manner that enhances the resolution and sensitivity of the reconstructed image.

SUMMARY OF THE INVENTION

The present invention satisfies this need by (1) recognizing that, contrary to expectations, resolution and sensitivity can be improved by decreasing the mean free path length of the measured energy travelling through the medium, (2) providing a method for enhancing the resolution and sensitivity by selecting wavelengths of energy that increase the total path length (i.e., minimum distance the energy must travel, expressed as multiples of the mean free path length) of the energy through the medium, and (3) providing a method for enhancing resolution and sensitivity by radially compressing the target medium in conjunction with wavelength selection.

It is one object of the present invention to provide a method for collecting data for use in image reconstruction of a target medium so that the resolution and sensitivity of the reconstructed image are enhanced. The method comprises providing a source and a detector, selecting one or more wavelengths of energy, directing the selected wavelength(s) of energy into the target medium and measuring the energy emerging from the target. Selecting the wavelength(s) comprises selecting one or more wavelengths of energy so that the total path length of the energy propagating through a target medium between a source and a detector is maximized.

It is a further object of the present invention to provide a plurality of detectors at a plurality of distances from the source and to select a plurality of wavelengths of energy, to enhance the resolution and sensitivity of the reconstructed image of the target. The plurality of wavelengths of energy are selected so that each of the plurality of wavelengths maximizes the total path length of energy between a source and at least one detector.

It is yet a further object of the invention to provide a method of selecting an optimal wavelength of energy to maximize the total path length. The method comprises providing a source and a detector, directing a wavelength of energy from the source into a target medium, measuring the emerging energy using at least one detector, and adjusting the wavelength of energy until the total path length is maximized, under the constraint that the energy density at the detector remains at an acceptably large value.

It is yet another object of the invention to further enhance resolution and sensitivity by radially compressing the target medium prior to wavelength selection, whereby compression of the tissue reduces the physical distance between a source and detector, and selection of an optimal wavelength increases the total path length so that resolution and sensitivity are increased.

BRIEF DESCRIPTION OF THE FIGURES

For a better understanding of the invention, together with the various features and advantages thereof, reference should be made to the following detailed description of the preferred embodiments and to the accompanying drawings, wherein.

DETAILED DESCRIPTION

As discussed above, the method of the present invention recognizes that, contrary to intuitive expectations, decreasing the mean free path length, for either absorption or scattering, of the imaging source energy through the target medium can improve resolution and sensitivity of the measured data and reconstructed images. The inventive method involves the selection of wavelengths of energy that increase the scattering and/or absorption coefficients of energy in the medium while maintaining a measurable and acceptable energy density at the detector for image reconstruction. A further aspect of the invention involves radially compressing the target medium in conjunction with wavelength selection to enhance resolution and sensitivity.

System

Figure 1:
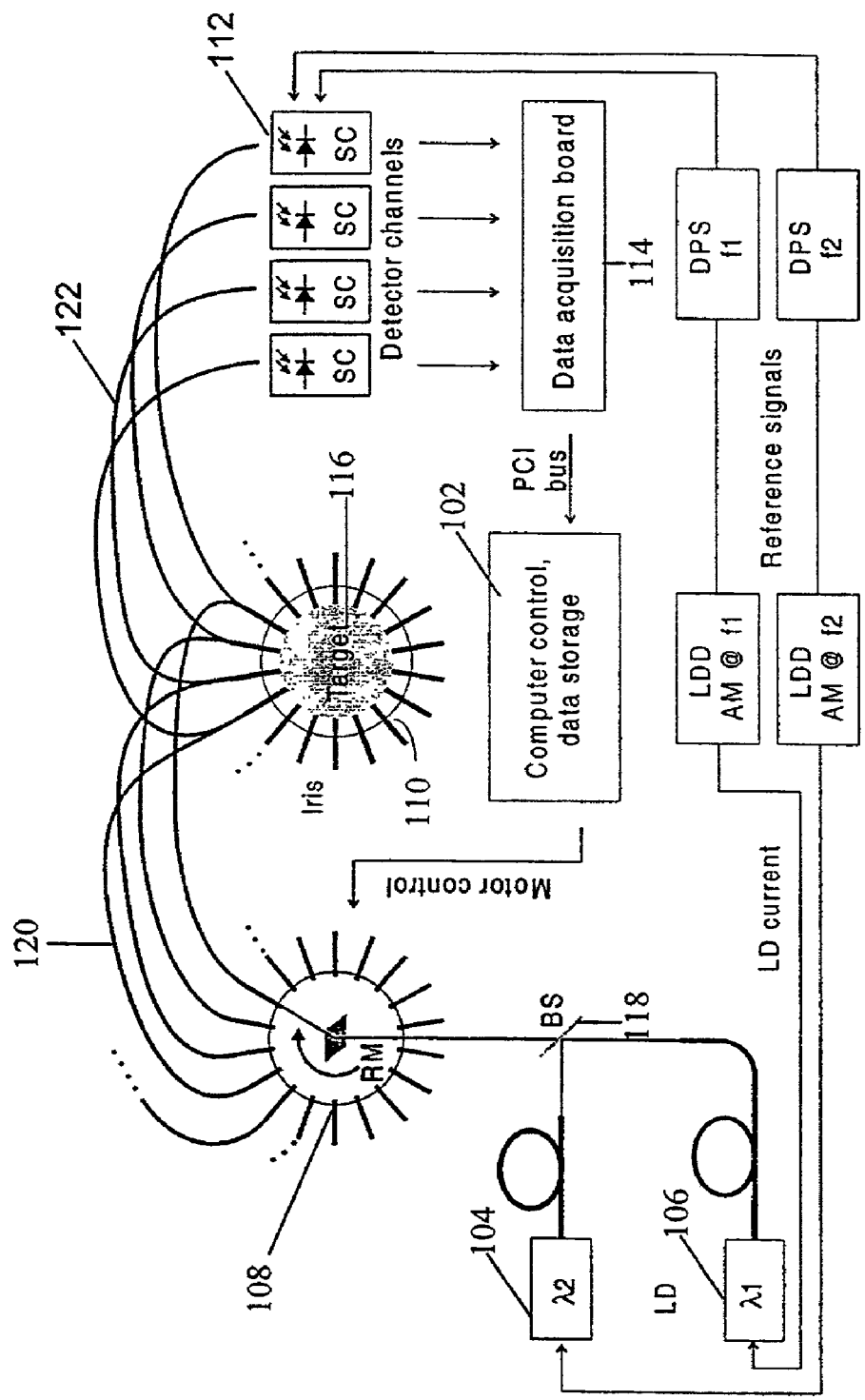
FIG. 1 is a schematic illustration of an exemplary imaging system.

Exemplary methods and systems for imaging of scattering media are disclosed in the "Barbour '355 patent, the "Barbour '322 patent, and the Barbour 4147PC2 application. A schematic illustration of one exemplary optical system is shown in FIG. 1. This system includes a computer 102, energy sources 104, 106, a source demultiplexer 108, an imaging head 110, detectors 112, and a data acquisition board 114.

A target 116 placed in the imaging head 110 is exposed to optical energy from the sources 104, 106. The optical energy originating from energy sources 104, 106 is combined by beam splitter 118 and is delivered to source demultiplexer 108. Although two energy sources 104, 106 are shown in this embodiment, an unlimited number of energy sources, each having a different wavelength, can be employed. Moreover, a single variable-wavelength energy source, such as a Ti-Sapphire laser or a tunable dye laser, can be used instead. The source demultiplexer 108, controlled by computer 102, directs the optical energy to source fibers 120 sequentially.

Each source fiber 120 carries the optical energy from the demultiplexer 108 to the imaging head 110, where the optical energy is directed into the target 116. The imaging head 110 contains a plurality of source fibers 120 and detector fibers 122 for transmitting and receiving light energy, respectively. Each source fiber 120 forms a source/detector pair with each detector fiber 122 in the imaging head 110 to create a plurality of source/detector pairs. The optical energy entering the target 116 at one location is scattered and may emerge at any location around the target 116. The emerging optical energy is collected by detector fibers 122 mounted in the imaging head 110.

The detector fibers 122 carry the emerging energy to detectors 112. The detectors 112 measure the intensity of the collected energy and generate a corresponding electrical signal. The data acquisition board 114 receives the signal, separates it by wavelength and samples and holds the separated signals for delivery to computer 102. The computer 102 in turn reads and stores the signal for image reconstruction.

This process is repeated, with energy delivered to each of the source fibers sequentially, and the emerging optical energy measured for each source/detector fiber pair. This process may continue over a period of time, with the computer 102 storing the data for reconstruction of one or more images. Additionally, the system may include two or more imaging heads for comparing one target to another. The computer 102 reconstructs an image representative of the internal optical properties of the target by using known perturbation methods to solve for the properties of the medium, such as absorption, scattering, florescence properties, and the like. It will be appreciated by those skilled in the art that more than one computer can be used to increase data handling and image processing speeds. The image reconstruction process may be any known technique, such as those disclosed in the Barbour '355 patent.

Wavelength Selection Method

The method of the present invention comprises the selection of a source energy wavelength producing the shortest mean free path length through the medium 116, from a source fiber 120 to a detector fiber 122, while maintaining an acceptable energy density at the detector 112. The mean free path length is the average distance a particle of energy travels between successive interactions with the medium 116 as it propagates from a source fiber 120 to a detector fiber 122. The total path length between a source and a detector is the ratio of the physical distance (e.g.; in centimeters) to the mean free path length, i.e., it is the distance between a source and a detector expressed in units of mean free path lengths.

The path an energy particle takes is a function of the absorption and scattering coefficients of the medium. The absorption and scattering coefficients are the inverse of the absorption and scattering mean free path lengths of the medium, respectively. These latter properties are the average distances a particle can travel through a medium before being scattered or absorbed. The absorption and scattering coefficients are functions of both position in the medium and of the source energy wavelength.

Figure 2:
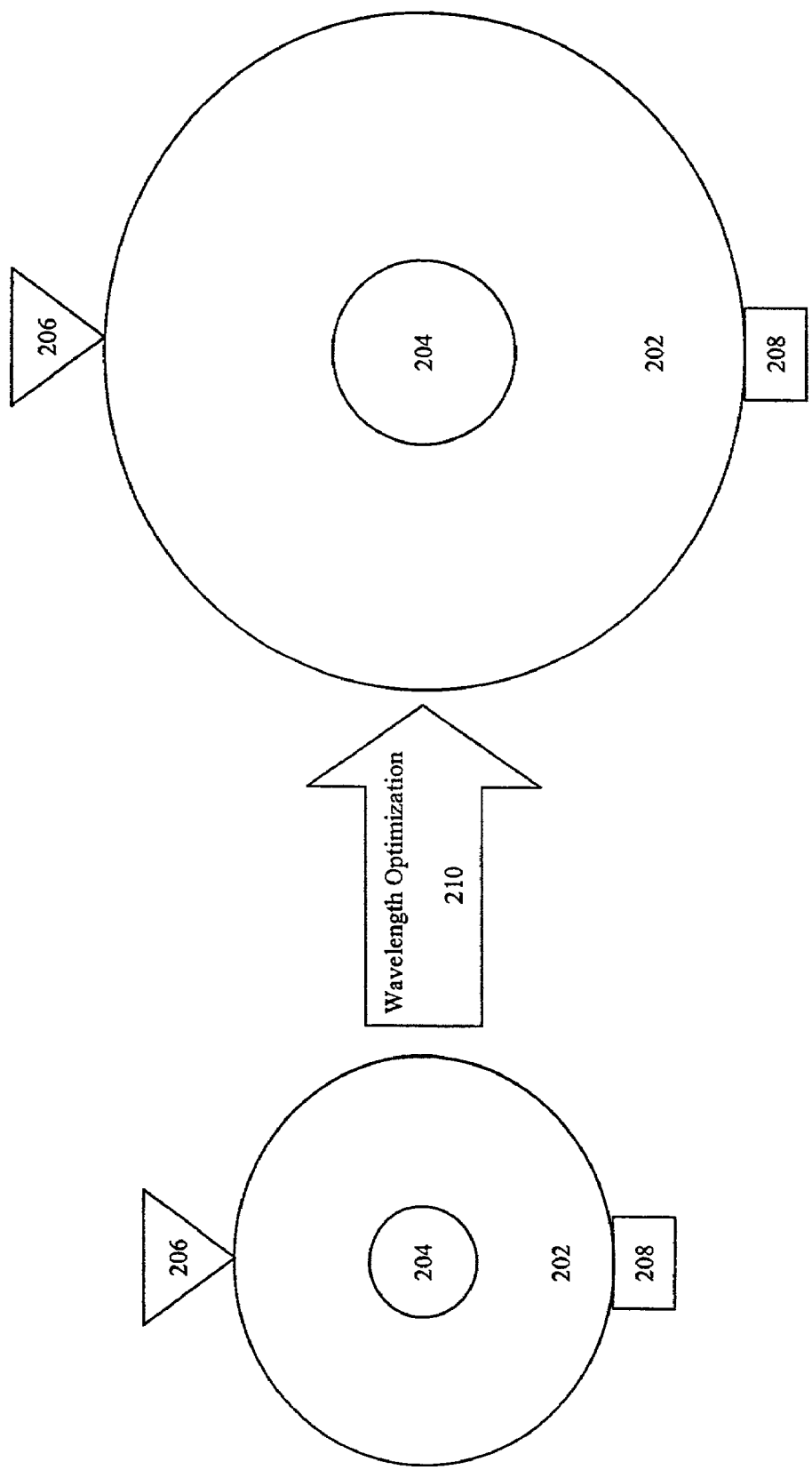
FIG. 2 is an illustration of an optimal wavelength approach.

As discussed above, the inventors of the present invention have discovered and make use of the counterintuitive phenomenon that the resolution and sensitivity of a reconstructed image can be increased by increasing the amount of scattering that energy undergoes as it propagates through a target medium 116. One way to increase scattering (and hence the total path length) is to increase the physical size of the target medium 116. However, this frequently is not a practical option. For example, the physical dimensions of living tissue, such as a human forearm, are not freely expandable. Accordingly, the method of the present invention recognizes that a "virtual" enlargement of the target can be created through adjustment of the wavelength of the imaging energy source. Referring to FIG. 2, a target medium 202 is illustrated having an included object 204. The target medium is shown at left in FIG. 2 in its physical size and at right in FIG. 2 in its "virtual" size after wavelength optimization 210. The result is that the total path length between source fiber 206 and detector fiber 208 has increased, so there has been a "virtual" enlargement of the target medium.

This "virtual" enlargement is realized because the total path length through the medium and the density of energy emerging from it are functions of the wavelength-dependent scattering and absorption coefficients. The shorter the scattering mean free path length, the more the energy particles are scattered, resulting in a longer total path length through the medium from a source to a detector. However, absorption also is a function of the total path length, with the probability of absorption increasing exponentially as the product of absorption coefficient and total path length increases. Accordingly, as the wavelength is adjusted to increase the total path length, there is more absorption of the energy particles and a lower energy density at the detectors.

Thus, there is a tradeoff between increasing total path length and maintaining acceptable energy density levels at the detectors.

By way of example, in a system for imaging a scattering medium using one wavelength of energy from a source and a plurality of detectors at different locations about the medium, the energy leaving the source will travel a different total path length to reach each detector. Referring back to FIG. 1, assume the source fiber 120 is located at the 12 o'clock position on imaging head 116. The source fiber 120 being at the 12 o'clock position, all energy particles will enter the medium from the source at the 12 o'clock position, but may exit at any of the detector fiber 122 locations arranged around the target 116. However, a particle that propagates through the medium to a detector fiber 122 at the 6 o'clock position is likely to have been scattered a far greater number of times and traveled a far greater total path length than a particle that exits at a position closer to the source fiber, such as a detector fiber at the 2 o'clock position.

As either the absorption or the scattering coefficient increases, the only photons that are likely to exit the medium into any given detector are those whose propagation paths lie close to the straight line joining the source to that detector. This preferential rejection of light that propagates from source to detector along paths other than the straight line increases the sensitivity of the detector to objects that straddle the source-to-detector line. Similarly, the reduced influence on the detector of structures that lie off this line implies a sharper transition from detectors that can "see" an inclusion to those that can not, i.e., improved spatial resolution. Therefore, given for example the empirical fact that for near infrared radiation in tissue both the scattering and absorption coefficients trend upward as wavelength decreases, a "virtual" enlargement of a tissue target can be accomplished simply by using a shorter illumination wavelength.

The method of the present invention may be used either to select a single optimal wavelength for single-wavelength systems, or a plurality of optimal wavelengths in multi-wavelength systems. Where a single wavelength is to be employed, it is selected so that the total path length is maximized while maintaining an acceptable energy density at the detector fiber that is most distant from the source fiber (in units of mean free path lengths through the medium). In this instance, because only one wavelength is available, the wavelength is optimized for the farthest detector.

Where multiple wavelengths are available, an optimum wavelength is selected for each detector or group of detectors, so that a plurality of wavelengths are selected, each wavelength being optimized for a single detector or group of detectors. In this way, the wavelengths are selected so that the total path lengths from the source to each detector are substantially equal at each detector's optimum wavelength.

The actual wavelength selection is preferably made empirically by a scout scan of the target medium, but it will be appreciated that the selection also could be made through rigorous solutions of the radiation transport equation. The scout scan is employed to determine the optimal wavelength (s) through a trial-and-error process. Where one source wavelength will be used for imaging, the trial and error scouting process includes incrementally adjusting the source wavelength until the energy density at any one of the detectors reaches the lowest acceptable level. Where multiple source wavelengths will be used for imaging, the preferred scouting method exposes the target medium to a series of wavelengths, the optimal wavelength for each detector being the wavelength for which the electrical signal generated by that detector reaches the lowest acceptable level.

For example, using optical energy in the near infrared region on human tissue, it is known that the absorption and scattering coefficients of the tissue increase with decreasing wavelength, and thus the total path length increases and the signals generated by the detectors decrease. Accordingly, selection of wavelengths using the scouting method could begin with a long infrared wavelength. The wavelength is then incrementally decreased, the optimal wavelength being selected for each detector as the wavelength is decreased. The optimal wavelength is the shortest wavelength before which the energy density at a detector falls to an unacceptably low level. Alternatively, the method may start with a short wavelength, incrementally increasing the wavelength and selecting the optimal wavelength for each detector when the energy density at the detector becomes acceptable. An acceptable signal at the detector is one for which the associated signal-to-noise ratio is above about 10.

Accordingly, in selecting a wavelength, a balance must be sought to optimize resolution and sensitivity against a declining energy density or signal level at the detectors. As a consequence, the optimal wavelength range can be expected to vary with the physical diameter of the medium. For example, in an imaging system employing primarily near infrared energy, a longer wavelength range (e.g., 800–700 nm) should be used for large diameter objects (10 cm–20 cm), whereas a shorter wavelength range (e.g., 600–700 nm) should be used for smaller diameter objects (2.5 cm–6.0 cm). In effect, for multiple-wavelength systems, a rainbow of light colors should be used and varied to enhance sensitivity and resolution, as indicated, in accordance with the target dimensions.

In order to maximize the resolution- and sensitivity-enhancing methods of the present invention, energy density from the source should be selected up to the acceptable limits of the medium being imaged. In this way energy densities at the detectors will be increased, permitting increased total path length and enhanced resolution and sensitivity.

A further aspect of the present invention is radial compression of the target medium. Like planar compression techniques, which apply compressive forces to opposing sides of the medium, radial compression reduces the physical distance through the medium between the source and detector by compression. Using planar compression techniques, the decreased physical thickness of the medium increases the energy density at the detectors but reduces the view angle over an embedded object within the medium. However, unlike planar compression, radial compression preserves a large view angle over an embedded object, at least where the embedded object also is compressible. The radial compression technique may then be combined with the wavelength-selection method discussed above to further enhance sensitivity and resolution.

Figure 3:
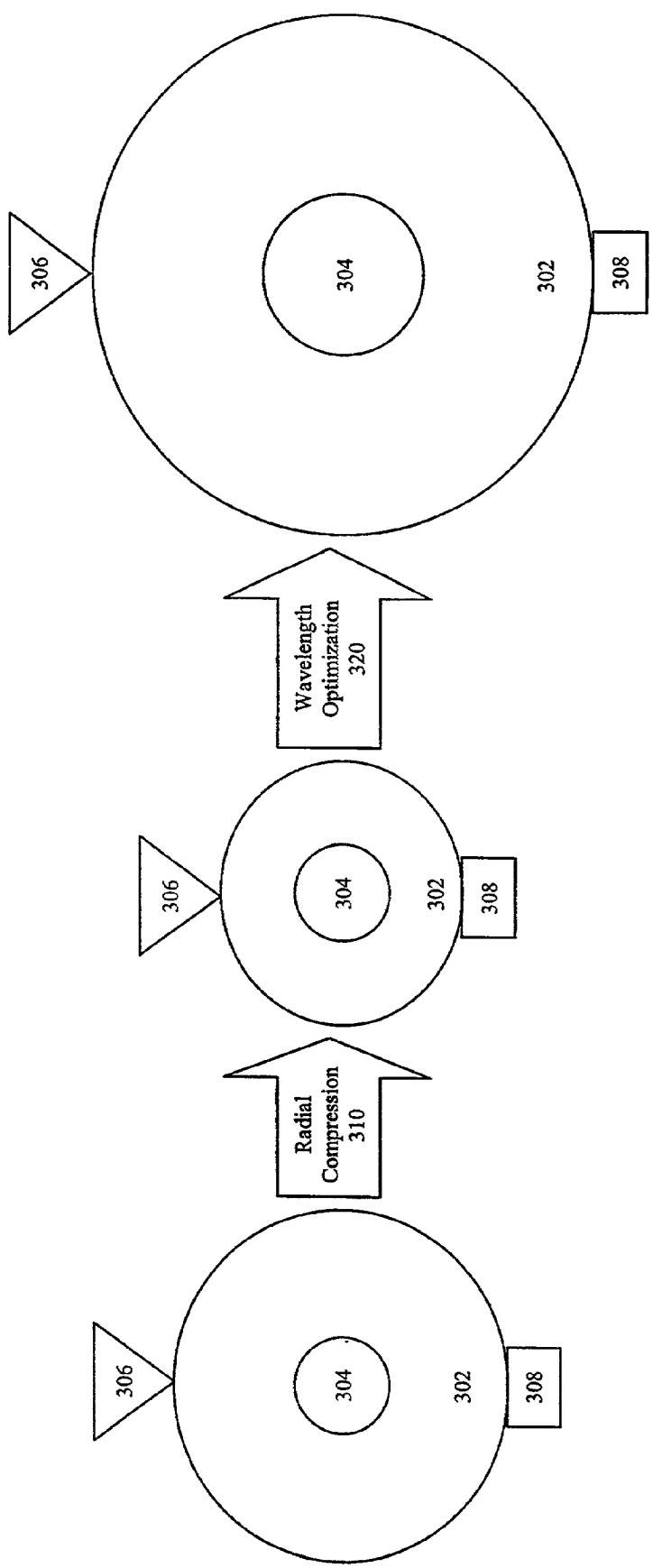
FIG. 3 is an illustration of a combination of radial compression and optimal wavelength approaches.

The approach of radial compression combined with optimal wavelength selection is illustrated in FIG. 3. In FIG. 3, the target medium 302 is a large breast containing a small tumor 304. A source 306 and detector 308 are positioned on the boundary of the target medium 302. Exerting mild radial compression 310 using any known means, such as those disclosed in the Barbour '099 application, the physical diameter of the target medium 302 is reduced, thereby increasing the energy density at detector 302. Depending on the compressibility characteristics of the tumor, imaging of the target medium in the compressed state will likely enhance sensitivity but decrease resolution of the tumor, at least in relative terms. However, by adjusting the source wavelength to select the optimal wavelength or wavelengths 320 as discussed above, the total path length through the target can be increased, thereby improving both sensitivity and resolution in absolute terms. This is illustrated as a virtual enlargement of the target medium 302.

Image reconstruction in both single- and multiple-wavelength systems may be accomplished by any known techniques, such as the SART or CGD methods. However, unlike single-wavelength methods for image reconstruction, the multiple-wavelength method of the present invention will generate a plurality of data sets based on the measured detector values for each wavelength. The most straightforward way to handle these data sets (i.e., the detector measurements) for each wavelength is to evaluate the data for each wavelength separately, followed by coalescing of results to produce a composite image. Formally, this requires solving a perturbation formulation of the radiation transport equation for each wavelength employed, using any of the known methods, such as those disclosed in the Barbour '355 patent.

While the multi-wavelength methods of the present invention may complicate data acquisition and analysis, a nearly ten-fold increase in sensitivity is observed upon an eight-fold increase in total path length.

Although the numerous examples above, and those to be discussed below, focus on near infrared energy sources for imaging human tissue, the methodology of the present invention is applicable with essentially any wavelength for any energy source (e.g., electromagnetic, acoustic, etc.), any scattering medium (e.g., body tissues, oceans, foggy atmospheres, geological strata, and various materials, etc.), and any source condition (e.g., time-independent, time-harmonic, time-resolved). Its applicability is dependent only on the presence of the phenomenology described herein, (i.e., diffusion being the principal mechanism of energy transport), which is expected in all cases where scattering occurs. Accordingly, this methodology can be extended to allow for new imaging approaches in a broad range of applications, including nondestructive testing, geophysical imaging, medical imaging, and surveillance technologies.

Experimental Validation

The following discussion presents results validating the relationship of increased total path length to enhanced resolution and sensitivity using a near infrared imaging system. These examples are presented merely as an illustration of the benefits of the optimized wavelength method of the present invention.

The analysis herein is described as it was used to determine the interdependencies of measurement parameters, such as view angle, wavelength and source location, and target parameters such as use of contrast agents, target geometry and size, background contrast, inclusion contrast and structural heterogeneity, as they relate to the sensitivity and edge resolution for a defined ROI. The analysis was divided into two parts: first, the exploration of homogeneous models with a centered inclusion simulating a tumor, and, second, examination of anatomically accurate optical (AAO) breast models, as defined by MRI data, containing a centered "tumor." The first is included primarily to differentiate the influence of geometry factors from effects of internal contrast features on the measured response. Its simplicity also facilitates focused laboratory investigations on phantoms for the purpose of verifying potentially interesting system performance features.

Figure 4B:
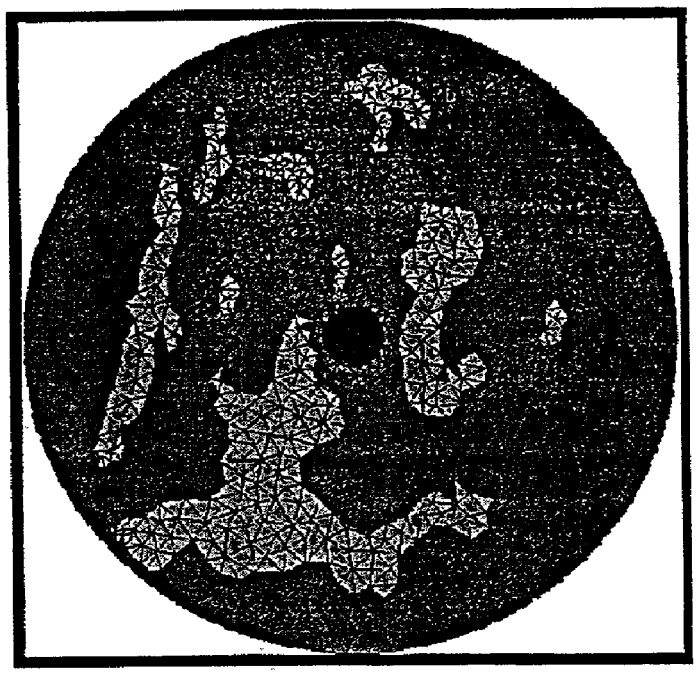
FIG. 4B is a finite element model (FEM) of the coronal slice in FIG. 4A.
Figure 4A:
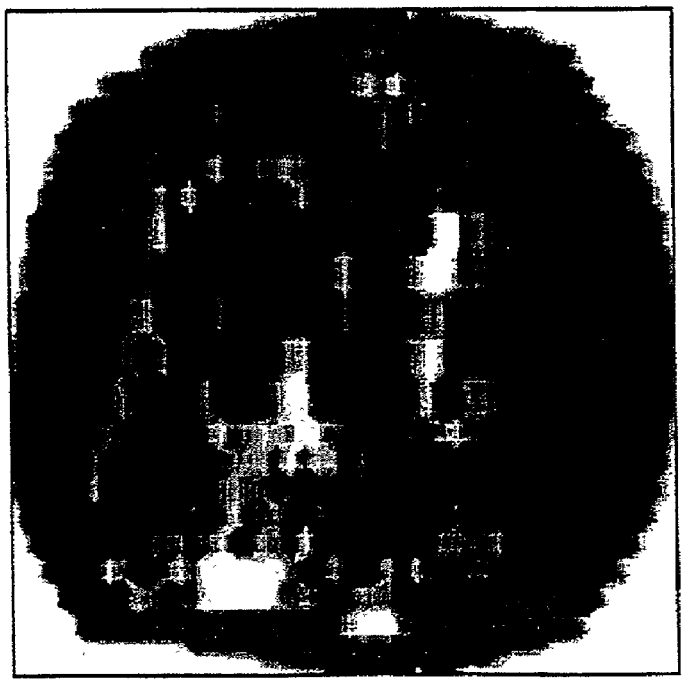
FIG. 4A is a reconstructed image of a coronal slice of a breast derived from MRI maps.

MR images of the breast were obtained using a GE Signa MRI system to develop a realistic model of the breast. The fast spin echo technique (TR=4000 ms, TE=112 ms, 3 mm thickness) was used, with and without fat and water suppression. A series of 24 sagittal images was obtained, and each image was subsequently converted into coronal views using the VoxelView image display program ("VoxelView 2.5 User's Guide," Vital Images, Inc. (www.vitalimages.com), 1995). The MRI breast maps were segmented using a semi-automatic image segmentation code provided by Chris Johnson from the University of Utah (H. W. Shen and C. R. Johnson, "Semi-automatic image segmentation: A biomedical thresholding approach," Technical Report UUCS-94-019, Dept. of CS, Univ. of Utah, 1994) (the disclosures of which are incorporated herein by reference). This code permits identification of user-defined outer and inner boundaries using a cubic spline data-fitting method. Referring to FIGS. 4A and 4B, FIG. 4A illustrates a representative coronal-view map (displayed at low resolution) FIG. 4B illustrates a corresponding representative finite element mesh of the map in FIG. 4A, with the introduction of a central inclusion simulating a tumor. The boundary geometries of the two maps differ because the external boundary of the breast was extended to conform to a circular geometry in the FEM model. This simplification was adopted to reflect the expected geometry that would exist for measurements of the breast using an imager that conforms the breast to a known circular shape.

Three different tissue types are identified in the MRI: adipose, parenchyma and the centrally positioned tumor shown in the FEM map. This central location was selected because it represents the region most difficult to detect. The extended region was assigned coefficients corresponding to adipose tissue. The segmented image served as the input file for FEM mesh generation. The mesh generation code, also provided by C. Johnson, uses the Delaunay tessellation algorithm originally proposed by Watson (D. F. Watson, "Computing the n-dimensional Delaunay tesselation with applications to Voronoi polytopes," *Computer Journal* 24(2), 167–172 (1981)). This algorithm was later extended by Weatherhill (N. Weatherill, and O. Hassan "Efficient three-dimensional grid generation using the Delaunay triangulation," Proceeding of the 1st European CFD Conference, 1 (1992)) (the disclosures of which are incorporated herein by reference). This code was implemented iteratively, with inspection of the generated mesh following each iteration to ensure construction of a mesh without any discontinuities between segmented regions.

The number of points and elements on the mesh used in the different models varied with breast size. For small diameters, the number of the points and elements was on the order of 1,500 and 3,000, respectively. For large diameters, these values were increased by as much as a factor of 15. An adaptive uniform refinement method was used to improve the efficiency of the FEM calculation for large-diameter maps (R. Beck, B. Erdmann and R. Roitzsch, "Kaskade 3.0—An object-oriented adaptive finite element code," Technical report TR 95-4, Konrad-Zuse-Zentrum für Informationstechnik, Berlin (1995)) (the disclosure of which is incorporated herein by reference). It is worth noting that whereas a variety of breast maps have been examined, the experimental validation described uses a single MRI map. Thus, the internal structural configuration of the background tissue is identical for all breast/tumor composite geometries explored. This was done for the purpose of differentiating the influence that variations in background/tumor contrast have on the measured parameters from effects caused by variations in the composite breast/tumor geometry.

Forward Model and Data Acquisition Geometry

The technique and method modeled light propagation in breast tissue as a diffusion process. For a domain $\Omega$ having a boundary $\partial\Omega$ and a DC point source, the diffusion process is represented by the expression:

$$\nabla \cdot [D(r)\nabla u(r)] - \mu_a(r)u(r) = -\delta(r-r_s), r \in \Omega$$

where $u(r)$ is the photon density at position $r$, $r_s$ is the position of the point source and $D(r)$ is the position-dependent diffusion coefficient, which is related to the absorption coefficient $\mu_a(r)$ and reduced scattering coefficient $\mu_s'(r)$ by $$D(r) = \frac{1}{3[\mu_a(r) + \mu_s'(r)]}$$

Light intensity values at the detectors were computed by applying Dirichlet boundary conditions on an extrapolated boundary. Depending on the breast size, the sources and detectors were positioned 1–2 transport mean free pathlengths below the extended surface. Solutions to the diffusion equation were computed by using the KASKADE adaptive finite element method. This is a publicly available code suitable for the solution of partial differential equations in one, two or three dimensions, using adaptive finite element techniques. For the purposes of the present invention, the basic code was modified to enable solutions to the diffusion equation with a point source.

Figure 5:
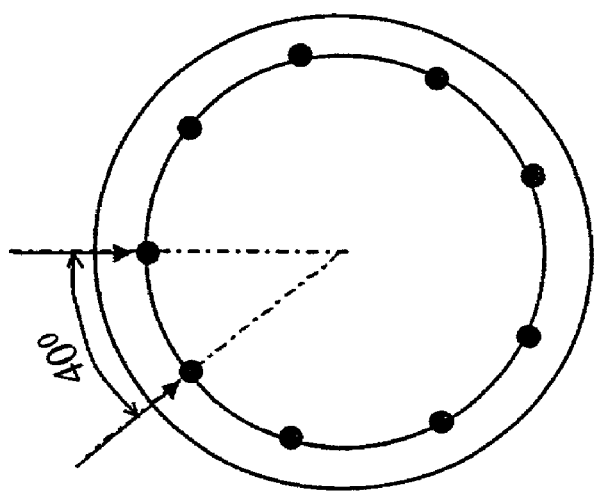
FIG. 5 is an illustration of the data acquisition geometry for a full tomographic view with 36 detectors in a uniform ring geometry, 9 detectors are illustrated.

FIG. 5 illustrates the data acquisition geometry. The arrows in the figure show two different locations of sources used for the reported results. Whichever of the two sources is adopted, the position of the detector corresponding to the source location is designated as 0°. The angular increment of the detectors was made in steps of 10° proceeding in a clockwise direction.

Definition of Sensitivity and Resolution

Sensitivity is defined as the relative intensity change between a defined target medium and a "background" medium from which the embedded object(s) is/are removed and replaced by material having the same properties as the bulk of the target medium. Thus, in the equation below, $u_t$ and $u_b$ represent the photon intensities produced at a detector by the target and by the background medium, respectively. Accordingly, the computed relative intensity change (i.e., sensitivity) is:

$$\delta_u = 1 - \frac{u_t}{u_b}$$

Figure 6:
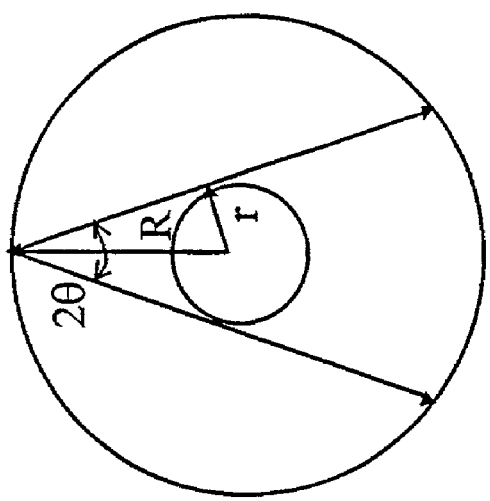
FIG. 6 is an illustration of the parameters used to define edge resolution.

Resolution is defined as the edge-spread function, corrected for the expected influence of the tumor geometry. Resolution is thus equal to the excess of the full-width at half-maximum (FWHM) of the sensitivity curve above its theoretical minimum value, (i.e., EFWHM=FWHM−FWHM$_{geom}$). Here, FWHM$_{geom}$=2 sin$^{-1}$(r/R), where r and R respectively are the radii of the centered inclusion and of the medium, as illustrated in FIG. 6. Therefore, a decrease in EFWHM signifies an improved resolution, whereas an increase in EFWHM means a loss of resolution. While this definition is valid, it is correct in absolute terms only in cases of comparisons between breast maps having the same diameter. On the other hand, in comparisons made among media of different diameters, a variation in the EFWHM is evidence of a change in the edge resolution relative to the size of the medium.

Parameter Space

The analysis examined the dependence of object sensitivity and edge resolution on four of seven principal parameters directly associated with the measurement and target domains. The corresponding dependences were inferrable for the other three parameters, because of known relationships among the seven. Principal parameters that were directly examined were variations in breast and tumor size, background tissue and tumor contrast, and the influence of view angle and source position. Inferred parameters were the impact of structural heterogeneity, choice of illuminating wavelength and use of contrast agents. In each case, the analysis considered a range of parameter values in an effort to better define their influence on the computed sensitivity and edge resolution.

Table 1 lists the diameters of the breast maps and tumors explored. These values were selected on the basis of the expectation that tumors can be located almost anywhere in the breast, from near the nipple to the chest wall, and that breast and tumor size obviously vary. For each of the seven breast diameters examined, the analysis additionally explored five different cross-sectional areas occupied by the tumor.

TABLE 1

Diameters of Breasts and Embedded Tumors

| Case # | Breast Diameter (cm) | Tumor Diameter (cm) [Corresponding to (Ratio of Tumor Cross-sectional Area to Breast Cross-Sectional Area) × 100] | | | | |
|---|---|---|---|---|---|---|
| | | 0.0625% | 0.25% | 1% | 2.25% | 4% |
| I | 16 | 0.4 | 0.8 | 1.6 | 2.4 | 3.2 |
| II | 12 | 0.3 | 0.6 | 1.2 | 1.8 | 2.4 |
| III | 10 | 0.25 | 0.5 | 1.0 | 1.5 | 2.0 |
| IV | 8 | 0.2 | 0.4 | 0.8 | 1.2 | 1.6 |
| V | 6 | 0.15 | 0.3 | 0.6 | 0.9 | 1.2 |
| VI | 4 | 0.1 | 0.2 | 0.4 | 0.6 | 0.8 |
| VII | 2 | 0.05 | 0.1 | 0.2 | 0.3 | 0.4 |

Table 2 lists the optical coefficients assigned to an embedded tumor. The values were selected based primarily on reports in the literature regarding observed optical properties of excised normal and cancerous breast tissue (T. L. Troy, D. L. Page, D. L. and E. M. Sevick-Muraca, "Optical properties of normal and diseased breast tissues: Prognosis for optical mammography," J. Biomedical Optics 3, 342–355 (1996)) (the disclosure of which is incorporated herein by reference). In some cases a more extended range was adopted, in order to explore the potential influence of contrast agents. For each of the composite breast/tumor sizes considered, the analysis considered the effect that variations in tumor contrast have on sensitivity and edge resolution. This parameter (i.e., variations in tumor contrast) was subdivided into three different contrast ranges. In two of these the scattering contrast was varied in the presence of moderate and high, but in either case fixed, absorption levels, and in the third the absorption was varied in the presence of a typical, fixed scattering value. In total, seven different contrast levels were explored.

TABLE 2

Optical Properties of Tumor Tissue

| Group | Case # | $\mu_a$ (cm$^{-1}$) | $\mu_s'$ (cm$^{-1}$) |
|---|---|---|---|
| (A) | 5, 6, 7 | 0.08 | 40, 20, 10 |
| (B) | 1, 2, 3 | 0.2 | 40, 20, 10 |
| (C) | 7, 3, 9 | 0.08, 0.2, 0.4 | 10 |
| (D) | 4, 8 | 0.2, 0.08 | 5 |

The range of contrast values assigned to the background tissues is shown in Table 3. Three different ranges of coefficient values were explored here, as well. These correspond to variations in the background absorption and scattering coefficients of the adipose tissue, and in the scattering coefficient of the parenchymal tissue. For comparative purposes we also explored the homogeneous state, as it represents the lower limit of contrast variation for the background tissues. In all, eight different background types were explored for each of the previously mentioned tumor contrast values. In total, the complete parameter matrix explored amounted to nearly 2,600 cases for each source location examined. The majority of these cases involved situations wherein the embedded tumor had higher absorption and/or scattering coefficient values than those of the background medium. It deserves emphasis that whereas we also have explored other MRI breast maps, all results reported here for inhomogeneous media are derived from a single MRI map.

TABLE 3

Optical Properties of Background Tissue

| Group | Case # | Adipose $\mu_a$ (cm$^{-1}$) | Adipose $\mu_s'$ (cm$^{-1}$) | Parenchyma $\mu_a$ (cm$^{-1}$) | Parenchyma $\mu_s'$ (cm$^{-1}$) |
|---|---|---|---|---|---|
| Homogeneous | 1 | 0.04 | 10 | 0.04 | 10 |
| (A) | 2, 3, 4 | 0.02, 0.04, 0.08 | 10 | 0.08 | 7 |
| (B) | 3, 7, 8 | 0.04 | 10, 15, 25 | 0.08 | 7 |
| (C) | 5, 6 | 0.04 | 10 | 0.08 | 15, 25 |

In review the results, the limiting case of contrast variation in breast maps with homogeneous backgrounds is considered first.

Influence of Target Size

Figure 7:
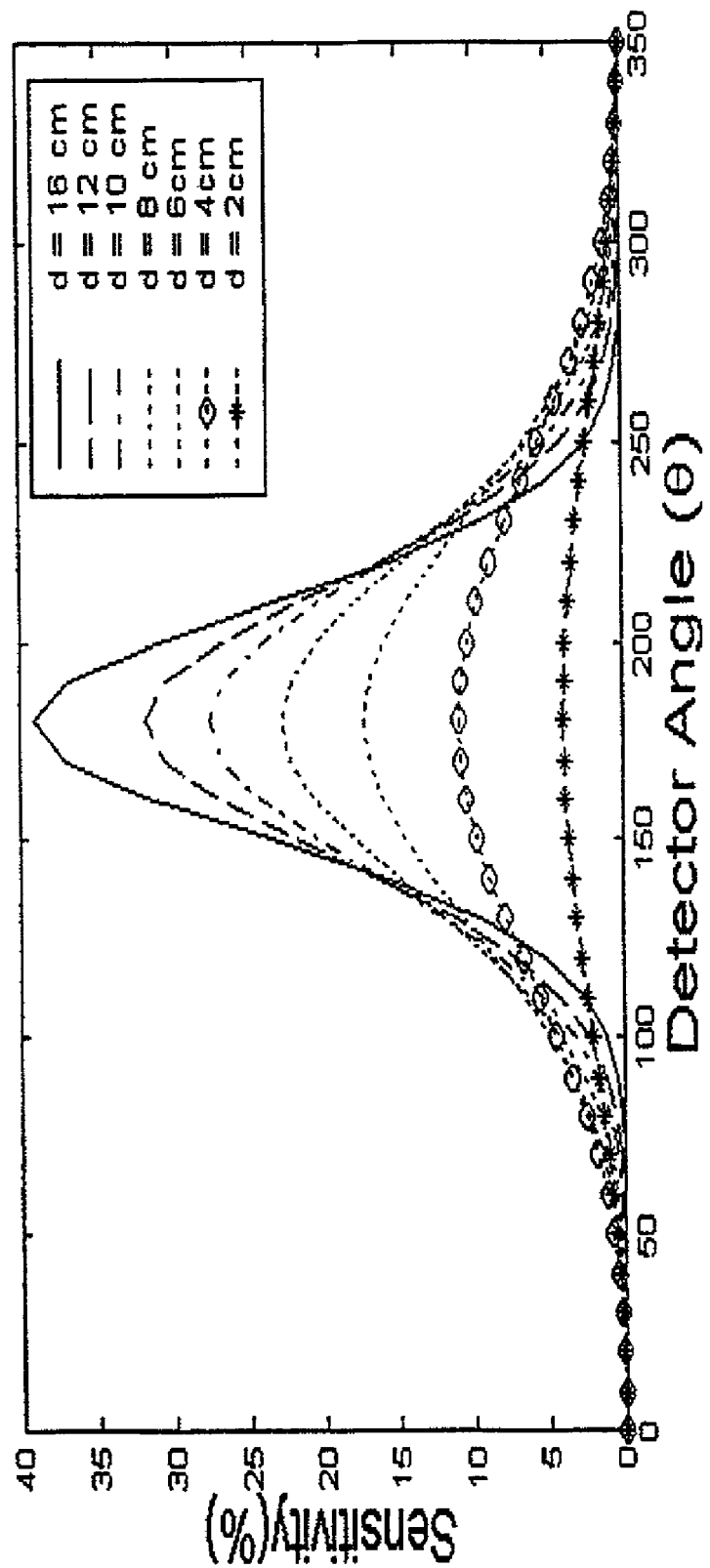
FIG. 7 is a graph plotting the percent change in relative sensitivity versus view angle for different target sizes.

The angular dependence of the relative intensity change on the size of the homogeneous background (i.e., breast) for a fixed inclusion (tumor) contrast value and fixed ratio of inclusion area to target area is shown in FIG. 7. The target diameter was varied between 2 and 16 cm to cover the expected range of diameters in the vicinity of the nipple and chest wall. The analysis shows that, contrary to what one might expect, the analysis shows that in all cases studied an increase in the total path length of the medium, corresponding to an increase in target size, significantly enhances the maximum relative intensity change observed at larger angular distances from the source. At intermediate angular distances, a biphasic response is observed (i.e., as the total path length increases, sensitivity at first rises, then falls).

Also shown in FIG. 7 is the seemingly counterintuitive finding of a reduction in the width of the sensitivity response curve with increasing target size. This indicates that an improvement in edge resolution accompanies the enhancement in sensitivity seen upon increasing the total path length. It is worth noting that these effects are not widely appreciated, although as shown elsewhere, they are predictable from theoretical considerations (H. L. Graber, R. Aronson, and R. L. Barbour, "Dependence of object sensitivity and resolution on optical thickness of scattering media," *J. Optical Society of America A*, submitted) (the disclosure of which is incorporated herein by reference). Also, note that because the comparison in sensitivity is between maps of different sizes, the enhancement seen in edge resolution is in relative terms. These responses are quantified in more detail in FIGS. 8A and 8B.

Effect of Composite "Breast/Tumor" Size on Sensitivity and Edge Resolution

Figure 8B:
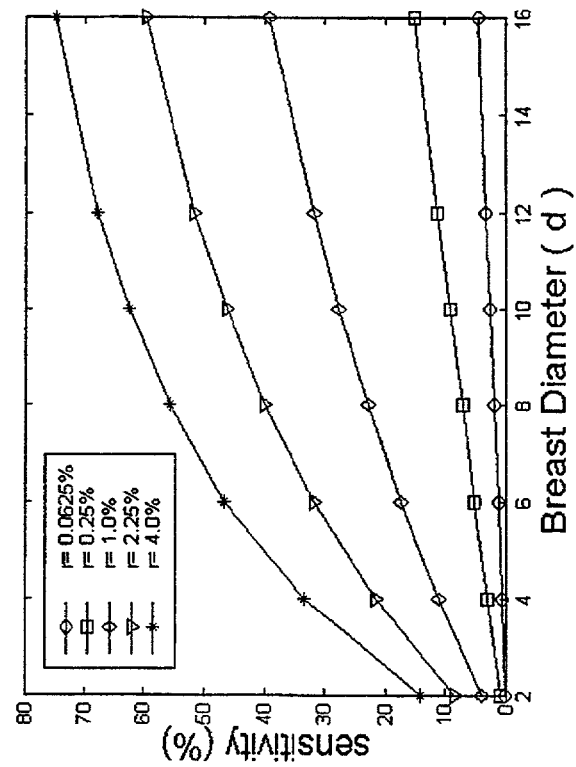
FIG. 8B is a graph plotting the percentage change in relative sensitivity versus the breast diameter for different cross-sectional area ratios.
Figure 8A:
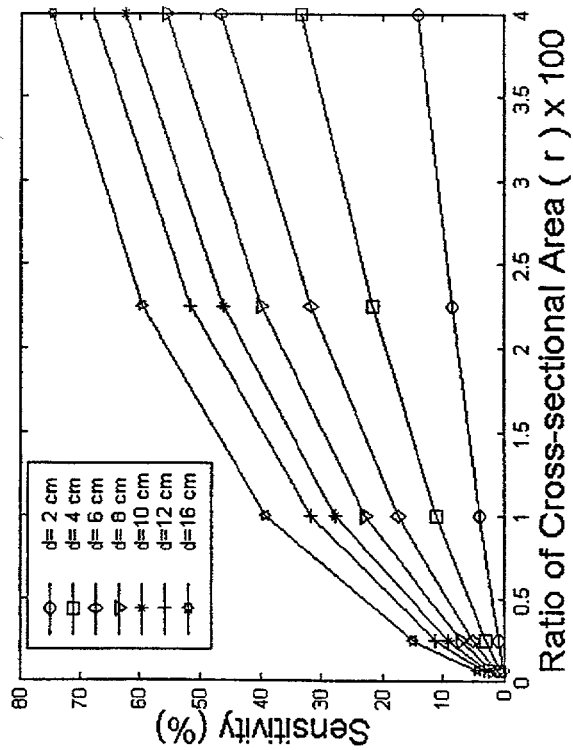
FIG. 8A is a graph plotting the percentage change in relative sensitivity versus the cross-sectional area ratio for different breast diameters.
Figure 9B:
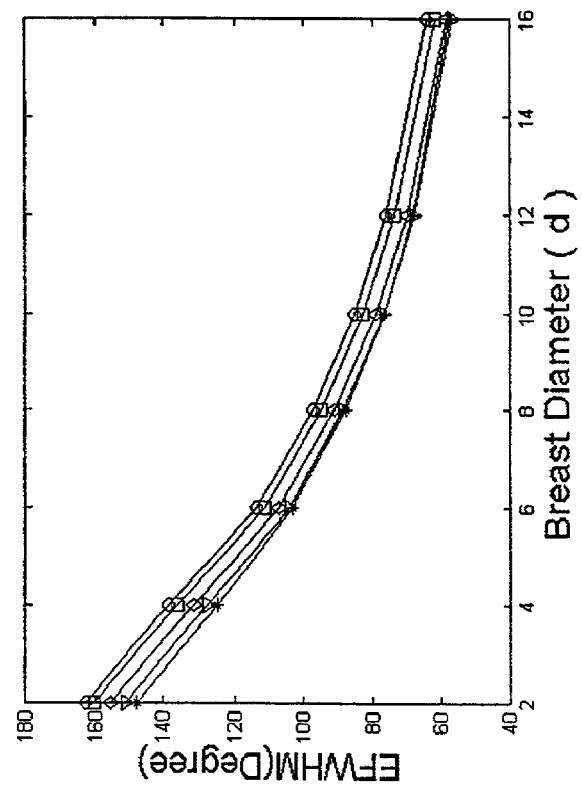
FIG. 9B is a graph plotting EFWHM versus the breast diameter for different cross-sectional area ratios.
Figure 9A:
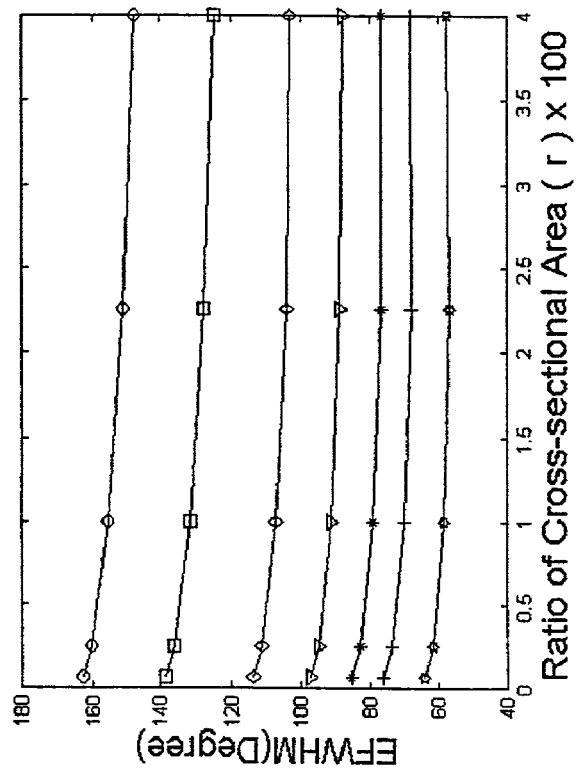
FIG. 9A is a graph plotting EFWHM versus the cross-sectional area ratio for different breast diameters.

Further examination of the above-described phenomenology is shown in FIGS. 8A and 8B, and 9A and 9B. Here the analysis has computed the maximum relative intensity change for a detector positioned 180° from the source (FIGS. 8A and 8B) and the corresponding excess of the full-width at half-maximum (EFWHM) (FIGS. 9A and 9B), as a function of the composite breast/tumor geometry, for a fixed tumor contrast. A comparison of results in FIGS. 8A and 9A shows that an increasing the ratio of the cross-sectional area of the tumor to that of the breast with the breast diameter fixed increases sensitivity significantly, especially for larger breast sizes (cf. FIG. 8A), and improves edge resolution slightly (cf. FIG. 9A). Results in FIGS. 8B and 9B demonstrate the corresponding response to variations in the breast diameter with a fixed ratio of cross-sectional areas. Again, a positive correlation is seen between sensitivity and target size when either one of the size parameters is fixed. Interestingly, the maximum rate of sensitivity change occurs when extreme values of the target geometry are paired. That is, the greatest change in sensitivity values occurs with large breasts containing small tumors (a clinically interesting case) (FIG. 8A) and small breasts containing large tumors (FIG. 8B). These findings indicate that sensitivity responses do not simply scale with target size.

Figure 10A:
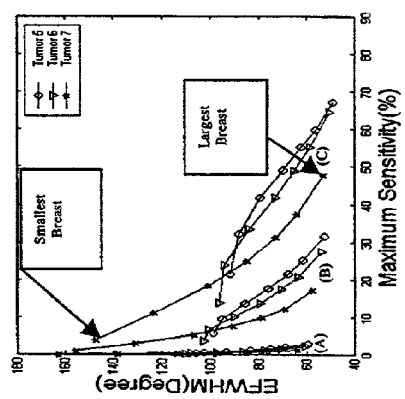
FIG. 10A is a graph plotting EFWHM versus the maximum sensitivity change caused by variations of breast and tumor size in homogeneous background media, where the absorption coefficient is fixed at 0.08 cm$^{-1}$ and the scattering coefficient varies from 10 to 40 cm$^{-1}$.
Figure 10B:
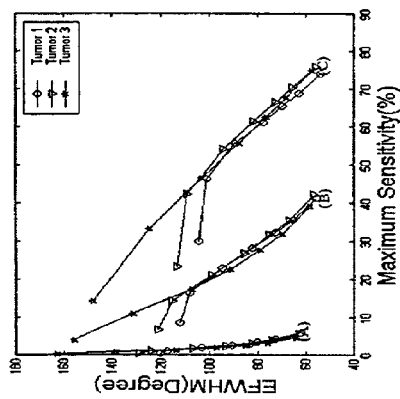
FIG. 10B is a graph plotting EFWHM versus the maximum sensitivity change caused by variations of breast and tumor size in homogeneous background media, where the absorption coefficient is fixed at 0.2 cm$^{-1}$ and the scattering coefficient varies from 10 to 40 cm$^{-1}$.
Figure 10C:
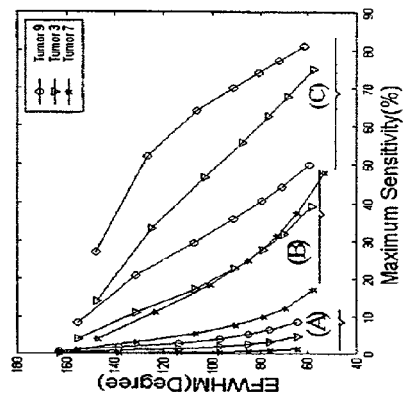
FIG. 10C is a graph plotting EFWHM versus the maximum sensitivity change caused by variations of breast and tumor size in homogeneous background media, where the scattering coefficient of tumor is fixed at 10 cm$^{-1}$ and the absorption coefficient varies from 0.08 to 0.04 cm$^{-1}$.

Influence of Composition of Target Geometry and Tumor Contrast on Sensitivity vs. Edge Resolution The results in FIGS. 10A through 10C show the EFWHM versus the maximum sensitivity for the detector positioned 180° from the source, as functions of breast size, tumor-to-breast area ratio and tumor contrast, for the different contrast groups. In FIGS. 10A and 10B the absorption coefficient of the tumor is fixed at 0.08 cm$^{-1}$ and 0.2 cm$^{-1}$, respectively, and the scattering coefficient varies from 10 to 40 cm$^{-1}$. In FIG. 10C the scattering coefficient of the tumor is fixed at 10 cm$^{-1}$ and the absorption coefficient varies from 0.08 to 0.4 cm$^{-1}$. Shown are the responses for three different area ratios (labeled A, B, and C, where A corresponds to 0.0625%, B to 1.0%, and C to 4%), as a function of breast diameter. For each line drawn, the maximum sensitivity increases monotonically with increasing breast diameter, while at the same time the EFWHM monotonically decreases.

Most striking is the strong dependence of edge detection and sensitivity on breast size, especially for the smaller tumors. In this case, an increase in breast size preferentially enhances edge resolution, independent of tumor contrast. Increasing tumor size (groups A through C) with the breast size and tumor contrast fixed primarily enhances sensitivity, although some enhancement in edge resolution is observed for larger tumors. Comparing results in FIGS. 10A through 10C illustrates the effect of varying tumor contrast. Results in FIG. 10A show that at moderate absorption values (i.e., 0.08 cm$^{-1}$), increasing the scattering contrast of the tumor preferentially enhances edge resolution for small breast sizes, while improving sensitivity for larger breast sizes. This differential response is most noticeable for breasts containing larger tumors. Results in FIG. 10B show that the sensitivity enhancement seen in large breasts when the scattering contrast of the tumor is increased is completely abolished upon increasing the absorption contrast of the tumor to 0.2 cm$^{-1}$. This shows that under the conditions examined, a four-fold enhancement in scattering contrast of the tumor has no additional influence on its detectability. Results in FIG. 10C show that the greatest improvement in sensitivity is observed upon an increase in the absorption of the tumor, with the largest effect occurring with larger tumors.

The next analysis considers an inhomogeneous background (i.e., the anatomically accurate optical (AAO) Breast Model).

Effect of Increased Background Scattering

Figure 11:
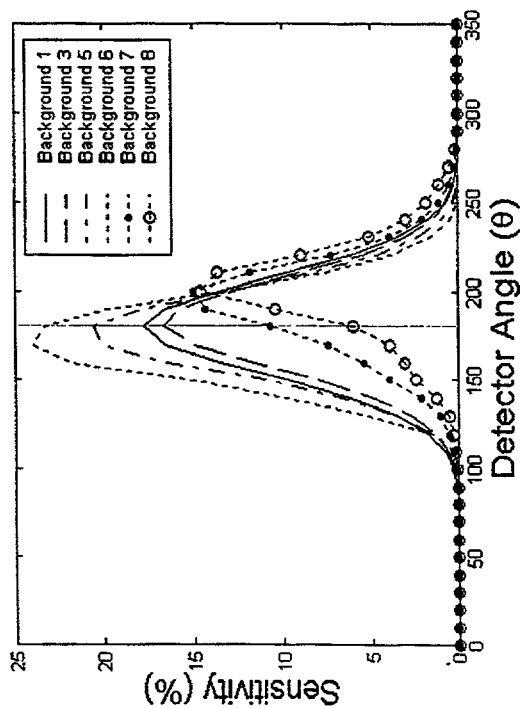
FIG. 11 is a graph plotting sensitivity versus view angle for different heterogeneous background media with a breast size of d=16 cm, tumor size of r=0.25%, and case 1 tumor contrast.

In this section the analysis considered results obtained from the AAO maps. The point of this analysis was to determine if the presence of an inhomogeneous background can appreciably influence the sensitivity or edge resolution obtained for the included tumor, relative to the homogeneous case. Results shown in FIG. 11 illustrate the effect that an increase in the difference between scattering coefficients of adipose and parenchymal tissue has on sensitivity, for the case of a small tumor (0.25% ratio of cross-sectional area) embedded in a large breast (16 cm). Specifically shown are responses seen for Groups B and C background media, which differ in the direction of the scattering contrast between the adipose and parenchymal tissues. For comparative purposes, the response seen for a homogeneous background also is shown. The most noticeable effect of background heterogeneity is a shift in the angle at which the greatest sensitivity is observed. Interestingly, the direction of this shift depends on the algebraic sign of the difference between the background tissues' scattering coefficients. The angle of maximum sensitivity is >180° when the adipose tissue is more strongly scattering than the parenchyma, and <180° when the parenchyma is the more strongly scattering. The ratio of maximum sensitivity to sensitivity at precisely 180° can be greater than 2:1, a result that highlights the limited value that restricted-view measurements can have for inhomogeneous media. Also seen in FIG. 11 is a marked reduction of the EFWHM for the medium having the largest scattering contrast between adipose and parenchymal tissues, especially for the Type-6 background, indicating improved edge resolution.

Not shown are results of similar analyses wherein the tumor size and contrast were varied as a function of background tissue contrast. In cases involving comparisons between media with similar tumor-to-breast area ratios, the influence of variations in tumor contrast, for a specified background, were mainly quantitative in nature. That is, in those situations where the above-described view-angle dependence of sensitivity on background scattering contrast was observed, it was largely independent of tumor contrast. This indicates that the observed behavior is primarily a function of the background contrast. Quantitatively, reduction in the absorption or scattering contrast of the included tumors predictably reduces measurement sensitivity. The influence of breast size on the angular response function is shown subsequently.

Influence of Breast Size

Figure 12:
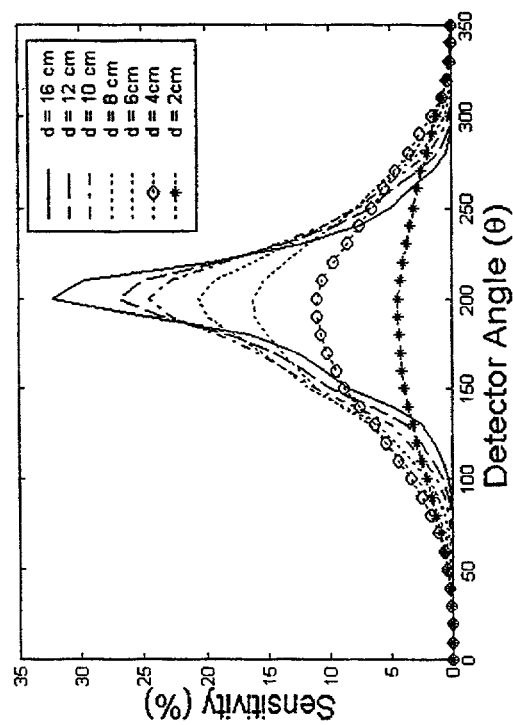
FIG. 12 is a graph plotting sensitivity versus view angle for different breast sizes, with case 3 tumor contrast and tumor size of r=1%, embedded in case 6 heterogeneous background medium.
Figure 13B:
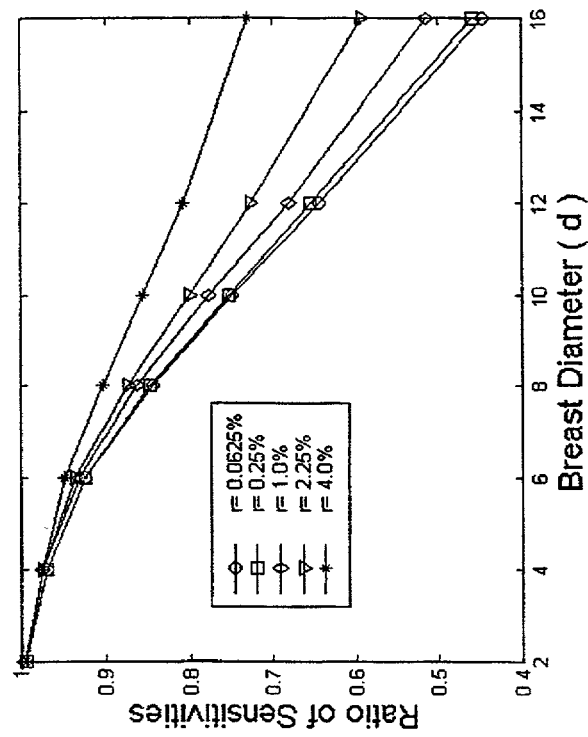
FIG. 13B is a graph plotting the ratio of sensitivity at 180° view angle to that at 200° view angle, versus the breast diameter for different cross-sectional area ratios, with case 6 heterogeneous background tissue and case 3 tumor contrast.
Figure 13A:
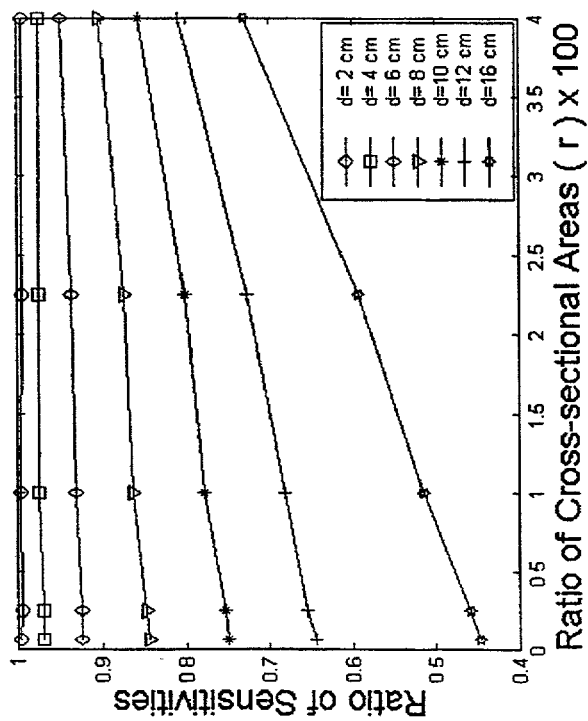
FIG. 13A is a graph plotting the ratio of sensitivity at 180° view angle to that at 200° view angle, versus the cross-sectional area ratio for different breast diameters.

The results illustrated in FIG. 12 show the effect on sensitivity of varying the breast size while holding the tumor-to-breast area ratio fixed, for a selected heterogeneous background medium (i.e., Case 6 background). A similar plot for the homogeneous background case was shown in FIG. 7. Comparison reveals that whereas the edge resolution improves with increasing breast size also in this heterogeneous case, its angular dependence is not a simple function of breast size. This absence of linear scaling between measured response and target geometry can be seen more clearly by comparing the sensitivities observed at 180° and at 200° view angles, as a function of the composite breast/tumor size. These results are shown in FIGS. 13A and 13B. In FIG. 13A the analysis shows a strong, nearly linear dependence of angular sensitivity on tumor size for large-diameter breasts but very little dependence for small-diameter breasts, even though the exact same heterogeneous background structures are present. FIG. 13B further shows that, in addition to this lack of scaling, the angular sensitivity dependence varies with tumor size, with the greatest dependence observed in the case of the smallest tumor embedded in a large breast (a clinically interesting case).

Influence of Source Location

Figure 14B:
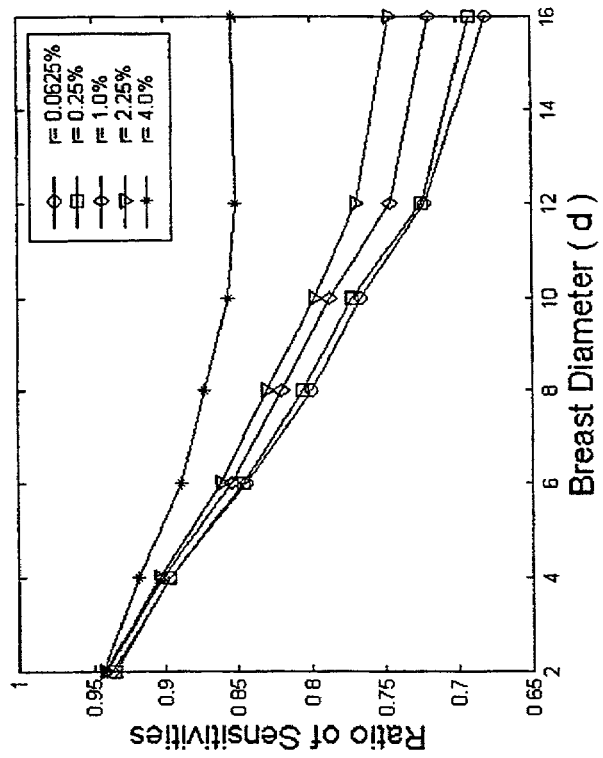
FIG. 14B is a graph plotting the ratio of the maximum relative intensity changes caused by source 1 ($\theta$=0°) and source 2 ($\theta$=−40°) versus the breast diameter, for different cross-sectional area ratios, with case 6 background tissue and case 3 tumor contrast.
Figure 14A:
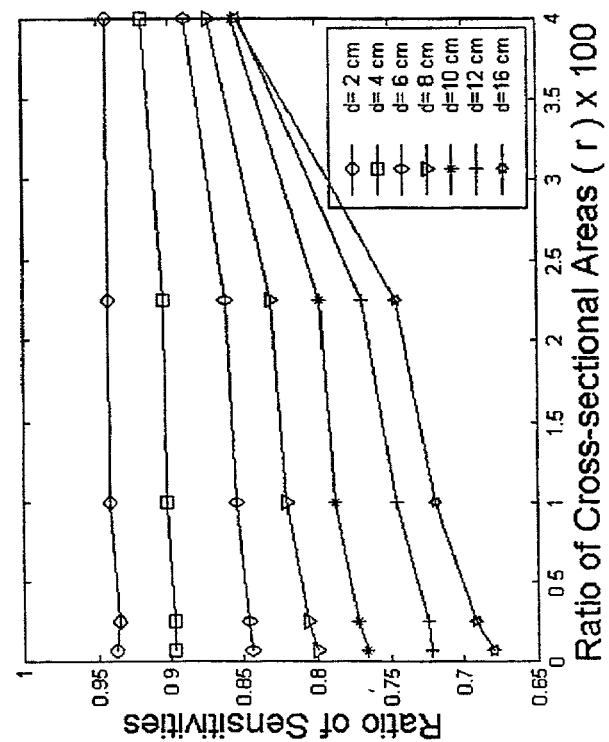
FIG. 14A is a graph plotting the ratio of the maximum relative intensity changes caused by source 1 ($\theta$=0°) and source 2 ($\theta$=−40°) versus the cross-sectional area ratio, for different breast diameters.

The results in FIGS. 14A and 14B show the dependence of the maximum sensitivity on source location (0° vs. −40°), as a function of the tumor cross-sectional area and the breast diameter, for background medium 6. This comparison is made to model how the source location influences the expected sensitivity of measurement for a heterogeneous medium, as a function of composite target geometry. Inspection of FIGS. 14A and 14B reveals trends similar to those observed in FIGS. 13A and 13B. Thus, whereas it is to be expected that varying the source position can influence measurement sensitivity for a heterogeneous medium, what is not obvious is that the magnitude of the differential response is dependent on the composite target geometry. The form of this dependence reveals an absence of scaling in sensitivity as a function of composite target geometry, even though identical background structures are present.

Figure 15B:
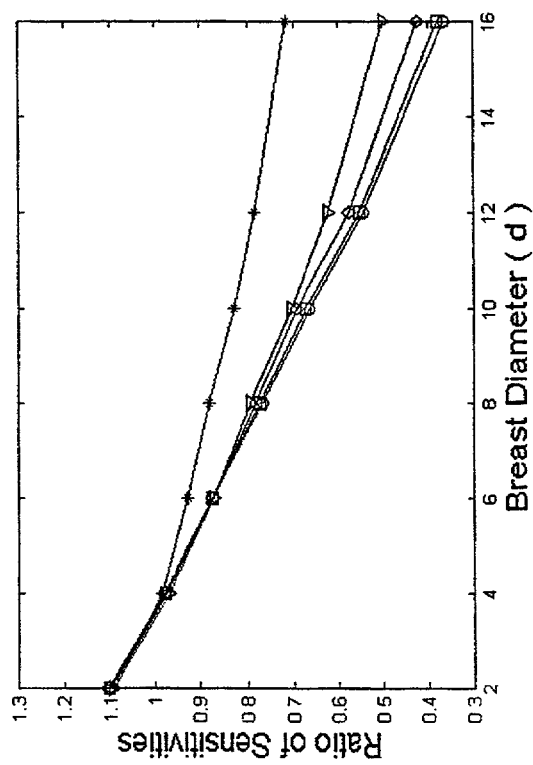
FIG. 15B is a graph plotting the ratio at 180° view angle, of relative sensitivity change for case 6 background medium to that for a homogeneous background medium (case 1), versus the breast diameter, for different cross-sectional area ratios, with case 3 tumor contrast (Definition of symbols provided in FIG. 8B)
Figure 15A:
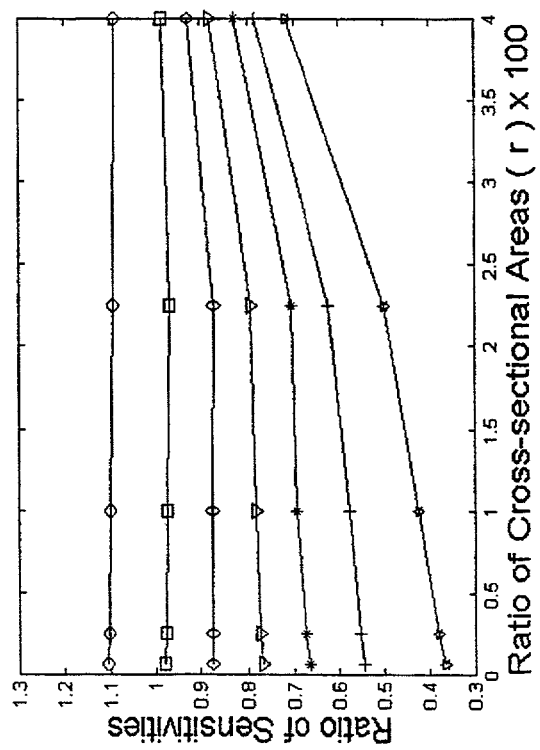
FIG. 15A is a graph plotting the ratio, at 180° view angle, of relative sensitivity change for case 6 background medium to that for a homogeneous background medium (case 1), versus the cross-sectional area ratio for different breast diameters (Definition of symbols provided in FIG. 8A)

Comparison of Sensitivity Dependence of MRI Breast Map to Homogeneous Background Results in FIGS. 11 through 14 identified the sensitivity dependencies of various measurement configurations for a fixed structural heterogeneity, as a function of background contrast and of composite target geometry. To complete our understanding, it is useful to isolate the influence of structural heterogeneity per se. This was investigated by comparing the measured responses for the case 6 background to those for a homogeneous background medium (case 1), as a function of composite target geometry, for a detector positioned opposite the source (i.e., 180° view angle). FIGS. 15A and 15B show the result for the case of type-3 tumor contrast, as a function of the composite target geometry. In FIG. 15A, we see that compared to the homogeneous case, the influence of structural heterogeneity on the detectability of the tumor varies strongly with breast size. For small-diameter breast maps, the presence of added contrast between the parenchyma and adipose tissues improves sensitivity to the tumor. However, the opposite effect is seen for larger diameter breasts, even though the identical structural heterogeneity and contrast difference is present in all cases, further demonstrating an absence of scaling in the measured response with target size. FIG. 15B shows a similar dependence when tumor size is varied.

Figure 16A:
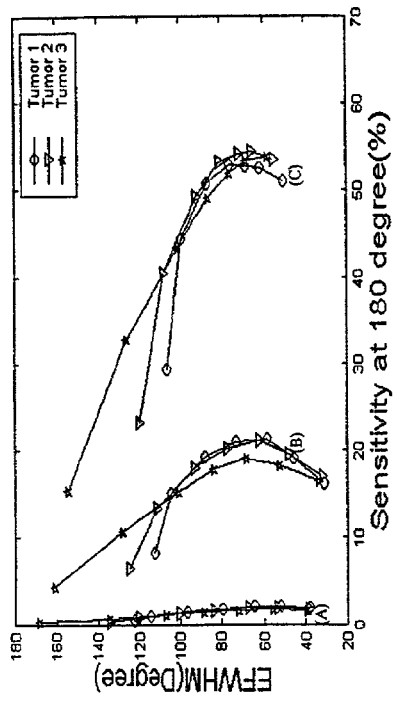
FIG. 16A is a graph plotting EFWHM versus sensitivity at 180° view angle for many combinations of breast size and tumor size, for a case 6 background medium and with the absorption coefficient fixed at 0.08 cm$^{-1}$ and the scattering coefficient varying from 10 to 40 cm$^{-1}$.
Figure 16B:
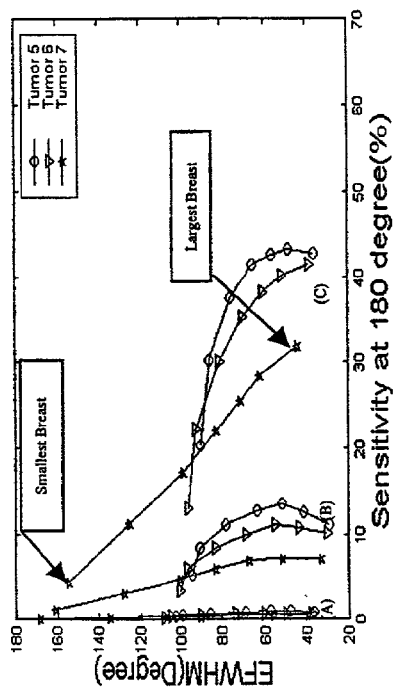
FIG. 16B is a graph plotting EFWHM versus sensitivity at 180° view angle, for many combinations of breast size and tumor size, for a case 6 background medium and with the absorption coefficient fixed at 0.2 cm$^{-1}$ and the scattering coefficient varying from 10 to 40 cm$^{-1}$.
Figure 16C:
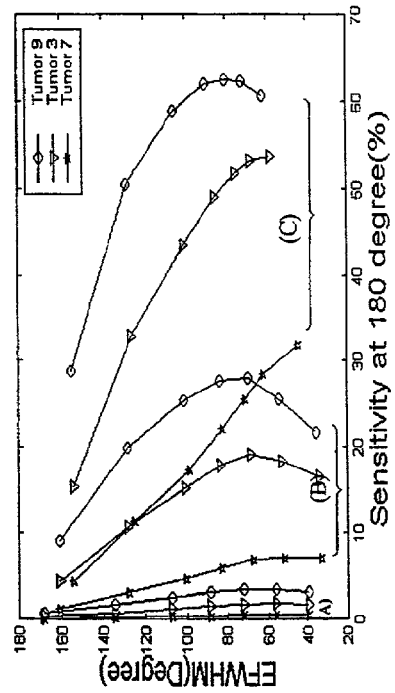
FIG. 16C is a graph plotting EFWHM versus sensitivity at 180° view angle for many combinations of breast size and tumor size, for a case 6 background medium and with the absorption coefficient varying from 0.08 to 0.4 cm$^{-1}$ and the scattering coefficient fixed at 10 cm$^{-1}$.
Figure 17B:
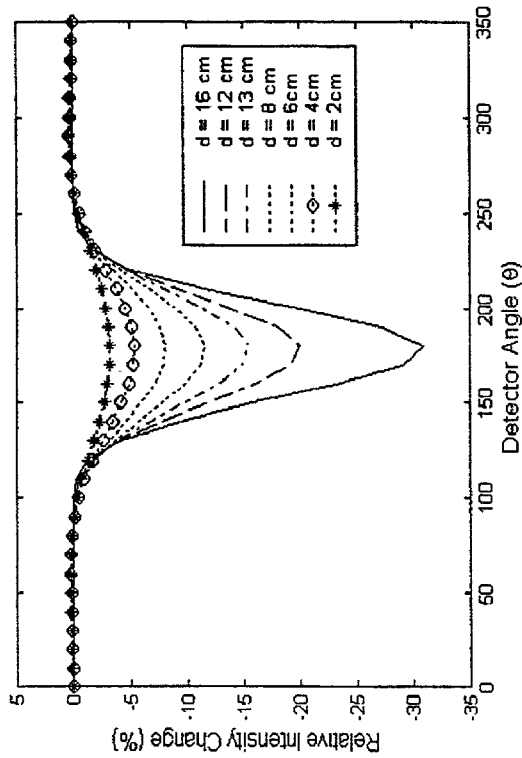
FIG. 17B is a graph plotting the percent relative change in intensity versus view angle for different breast diameters, with case 8 tumor contrast, tumor-to-breast area ratio r=1%, and case 4 background media.
Figure 17A:
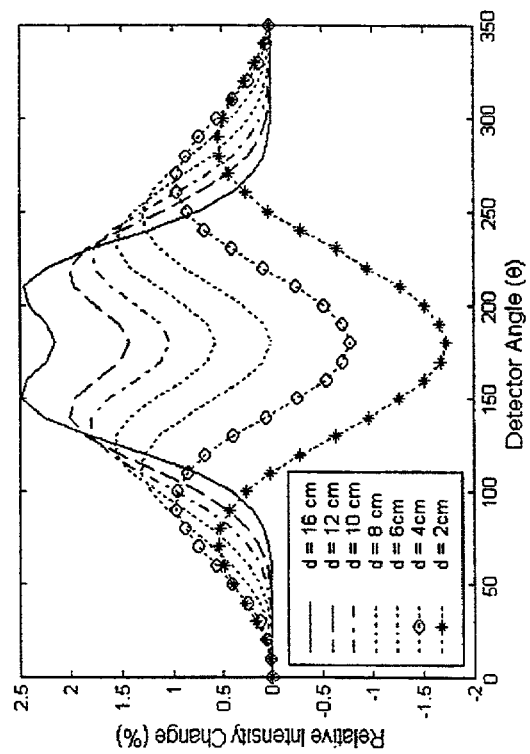
FIG. 17A is a graph plotting the percent relative change in intensity versus view angle for different breast diameters, with case 8 tumor contrast, tumor-to-breast area ratio r=11%, and homogenous background media.
Figure 17D:
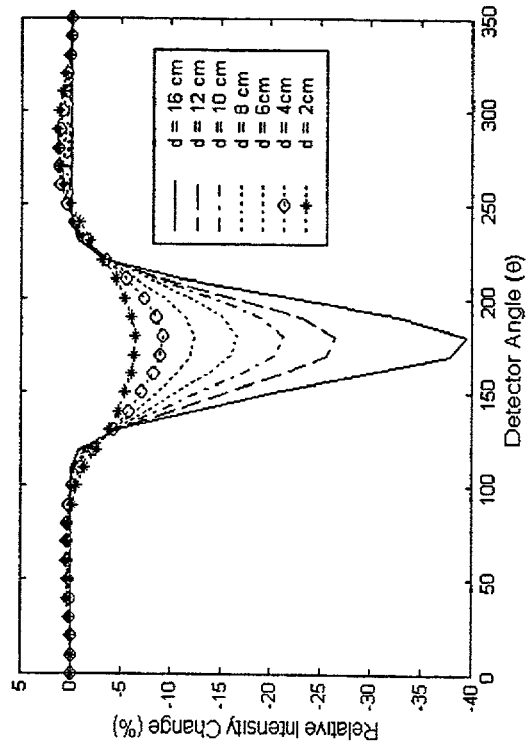
FIG. 17D is a graph plotting the relative change in intensity versus view angle for different breast diameters, with case 8 tumor contrast, tumor-to-breast area ratio r=1%, and case 8 background media.
Figure 17C:
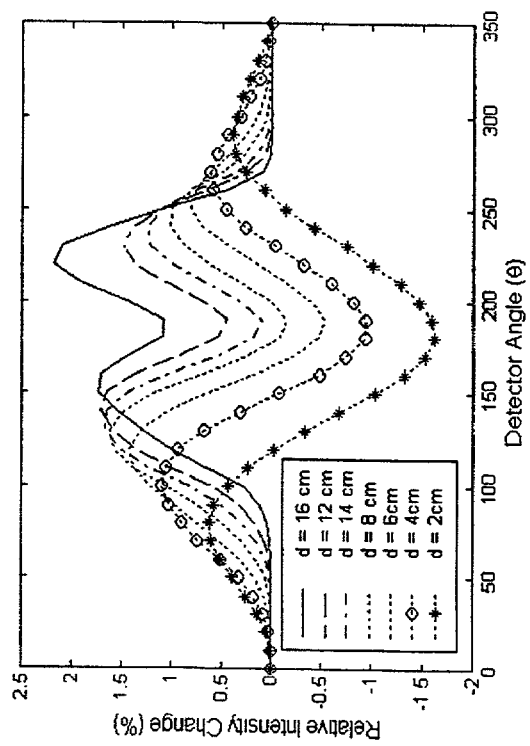
FIG. 17C is a graph plotting the percent relative change in intensity versus view angle for different breast diameters, with case 8 tumor contrast, tumor-to-breast area ratio r=1%, and case 5 background media.

Influence of Composition of Target Geometry and Tumor Contrast on Sensitivity vs. Edge Resolution The results in FIGS. 16A through 16C show the effects of variations in the target geometry on EFWHM and on relative sensitivity at the 180° view angle, for the three tumor contrast ranges and a selected inhomogeneous background (i.e., type 6). A similar study for a homogeneous background is shown in FIGS. 10A through 10C. Comparison of data in FIGS. 10 and 16 reveals that while qualitative similarities are present, overall a more complex response is seen in the heterogeneous case. Most notable is that portions of some of the EFWHM vs. sensitivity relations are not single-valued functions, revealing that in these cases maximum sensitivity is achieved at some intermediate breast size. Also different is the loss of edge resolution with increasing tumor size, especially in the case (FIG. 16C) of variable tumor absorption coefficient. It is worth noting that results presented in FIG. 16 do not coincide with the position of maximum sensitivity, which as shown in FIG. 12, occurs at a ~200° view angle from the source. A similar analysis at this view angle (results not shown) produced trends closer to those observed for a homogeneous medium. This suggests that background heterogeneity per se does not fundamentally limit the achievable edge resolution and sensitivity, but instead alters the location where they can be attained.

Response to Reduced Contrast Tumors

The results presented in the preceding figures emphasize mainly the influence that the various parameters have on the computed responses for tumors having higher absorption and scattering coefficients than those of the surrounding background medium. In FIGS. 17A through 17D, we examine the corresponding responses for a case in which a tumor is more weakly scattering than the background, for different breast sizes, and compare this to the homogeneous case. Overall, we see that while in many cases a more complex profile is observed, the trend favors improved sensitivity and improved edge detection with increased breast size.

Summary of the Principal Results

An important phenomenon observed in the results presented is that for any tumor-to-breast area ratio, tumor contrast and background medium contrast, the maximum sensitivity and edge resolution both increase significantly as the breast diameter increases. Also observed is that increasing the tumor size, for a fixed tumor contrast and breast size, increases sensitivity and, to a lesser extent, edge resolution (cf. FIGS. 9, 10 and 16). In addition, increasing the absorption contrast of the tumor alone increases sensitivity, but does not improve edge resolution (cf. FIGS. 10, 16).

We also observed that the effect of varying the scattering contrast of the tumor on sensitivity and edge resolution is a function of composite target size as well as of the absorption contrast of the tumor (cf. FIGS. 10, 16). For small breasts, sensitivity and edge resolution are improved simultaneously as the scattering contrast of the tumor increases, but there is a larger change in sensitivity for small breasts with a large tumor. For large breasts the effects on edge resolution and sensitivity are different, such that increases in the scattering contrast of the tumor improves sensitivity alone, but only with tumors having moderate absorption contrast.

In all, a consistent finding throughout all the variations explored is the absence of scaling of the measured response with target size. Specifically, we mean that trends observed in edge resolution and sensitivity as a function of tumor contrast, size and background contrast do not extrapolate to media of larger sizes, even though the exact same distribution of internal contrast and tumor size relative to background medium is present. These findings not only provide a comprehensive understanding of expected measurement performance associated with the two types of parameter spaces explored, (i.e., measurement and target domains), but also provide a guide to identifying the optical measurement strategies required to obtain optimal sensitivity and resolution. In the following, we extend these observations and discuss complementary strategies that can optimize achievable sensitivity and resolution.

Discussion

We have systematically explored the parameter domains associated with the target properties and measurement conditions, for the purpose of gaining insight into the relationships between these domains and their possible influence on the design of practical imaging systems. Two critical parameters that should be kept in mind when designing such systems are expected limits on sensitivity and resolution. Without a doubt, an important factor influencing these limits will be the view angle of measurement. In the case of imaging studies on the breast, several options are available, some of which have been adopted without rigorous proof that they are best suited for achieving optimal sensitivity and resolution.

One design in particular that has been implemented is a raster scan with a single detector positioned 180° opposite the source, with the breast subjected to mild planar compression. While compression of the breast will improve signal levels, it will be at the expense of a restricted view. Results in FIG. 12 show that, depending on the optical properties of the background tissues and their distribution in relation to a region of interest (ROI), sensitivity to a centrally located structure can vary several-fold over an angle of 20°. Since details of the underlying structural heterogeneity of the breast are unknown a priori, the influence of such structures on sensitivity can be expected to vary significantly. At a minimum, this observation suggests that the presence of heterogeneous backgrounds in the breast will severely limit efforts to obtain reproducible results from measurements employing restricted views. This would be especially true should serial measurements be performed, in which case the plasticity of the breast would surely undermine efforts to reproduce precise positioning of the tissue.

Our results suggest that improved reproducibility should be achievable using measurement schemes that employ broader views, because background heterogeneity can shift the location where optimal sensitivity is achieved. The difficulty with this approach is that it may limit the ability to use planar compression schemes. As indicated, while it is clear that compression of the tissue will improve signal levels, it is worth examining whether this is accompanied by improvements in sensitivity and resolution. Although planar compression geometries were not specifically investigated in this study, we believe that comparison of results from the different breast sizes can nevertheless provide insight into the expected influence of such geometries on these parameters.

Comparison of results for different model diameters is equivalent to imposing radial compression on the tissue, because the internal features of the different breast models studied are identical to a first approximation. Table 4 lists results derived from FIGS. 8A and 8B, and 9A and 9B, where the expected influence of a radial compression maneuver on sensitivity and edge resolution of the tumor is examined assuming different compression responses of an included tumor. For simplicity, expected out-of-plane effects of tissue/tumor compression are ignored. Considered is a large breast (16 cm) containing a tumor whose size (1.6 cm) is 1% of the total cross-sectional area. These results show that use of compression techniques is always accompanied by a loss of resolution due to reduced breast size, while its effect on sensitivity depends on the degree of compressibility of the tumor with respect to the surrounding tissue. In the case where the tumor has compressibility similar to that of the surrounding media, radial compression of the tissue from 16 cm to 10 cm diameter causes a 29% and 35% loss of sensitivity and edge resolution, respectively. These values compare to corresponding declines of 16% and 34% for the case of partial tumor compression, and to a 25% gain in sensitivity coupled with a 31% loss of resolution for an incompressible tumor. These results show that tissue compression per se does not guarantee improvement in sensitivity and resolution, and frequently can make matters worse.

TABLE 4

Influence of a Radial Compression Maneuver on Sensitivity and Edge Resolution

| Items | Before Compression | After Compression | | |
|---|---|---|---|---|
| Breast Diameter (cm) | 16 | 10 | | |
| Tumor Diameter (cm) | 1.6 | 1.0 (Proportionally Changed) | 1.4 | 1.6 (Completely Unchanged) |
| Tumor-to-Breast Area Ratio (%) | 1 | 1 | 1.96 | 2.56 |
| Maximum Sensitivity (%) | 39.1 | 27.6 (↓ 29.4%) | 33.0 (↓ 15.6%) | 49.0 (↑ 25.3%) |
| Resolution (EFWHM) (Degrees) | 58.36 | 78.92 (↓ 35.2%) | 78.11 (↓ 33.8%) | 76.73 (↓ 31.48%) |

Although illustrative embodiments have been described herein in detail, those skilled in the art will appreciate that variations may be made without departing from the spirit and scope of this invention. Moreover, unless otherwise specifically stated, the terms and expressions used herein are terms of description and not terms of limitation, and are not intended to exclude any equivalents of the system and methods set forth in the following claims.

What is claimed is:

1. A method for collecting data for use in image reconstruction of a scattering target medium, comprising:
   providing a source for directing at least one wavelength of near infrared energy into a target medium;
   providing a detector for measuring diffusely scattered near infrared energy emerging from the target medium;
   selecting at least one wavelength of near infrared energy, wherein the at least one wavelength of near infrared energy is selected to maximize the total path length of near infrared energy propagating through the target medium from the source to a detector and to maintain an acceptable energy density at the detector;
   directing at least one selected wavelength of near infrared energy into the target medium; and
   measuring at least one wavelength of diffusely scattered near infrared energy emerging from the target medium;
   providing a plurality of detectors at a plurality of distances from the source, and
   selecting a single wavelength to maximize the total path length of near infrared energy from the source to a detector furthest from the source and to maintain an acceptable energy density at the farthest detector.

2. The method of claim 1, wherein the total path length is the sum of a plurality of total mean free path lengths a particle of near infrared energy travels as it propagates through the medium from the source to a detector.

3. The method of claim 1, wherein a single detector is provided.

4. The method of claim 1, wherein the farthest detector is the detector having lowest energy density measurement among the plurality of detectors.

5. The method of claim 1, wherein the farthest detector is the detector detecting the diffusely scattered near infrared energy having the longest total path length among the total path lengths of the energy propagating from source to each of the plurality of detectors.

6. The method of claim 1, wherein a plurality of different wavelengths are selected, each of the plurality of wavelengths being selected to maximize the total path length of near infrared energy from the source to a detector and to maintain an acceptable energy density at the detector.

7. The method of claim 1, wherein selecting at least one wavelength comprises:
   directing a wavelength of near infrared energy into the target medium;
   measuring the emerging diffusely scattered near infrared energy from the target with at least one detector;
   adjusting the wavelength of the near infrared energy based on the measured emerging diffusely scattered near infrared energy to maximize the total path length and to maintain an acceptable energy density at a detector; and
   selecting at least one wavelength of near infrared energy having a maximized total path length from the source to at least one detector and an acceptable energy density at a detector.

8. The method of claim 7, wherein the wavelength is adjusted to increase the total path length and decrease the energy density at a detector.

9. The method of claim 7, wherein the wavelength is adjusted to decrease the total path length and increase the energy density at a detector.

10. The method of claim 7, wherein the adjusting step is repeated until a wavelength is selected.

11. The method of claim 7, wherein the adjusting step is repeated until a plurality of wavelengths are selected.

12. The method of claim 1, further comprising radially compressing the target medium.

13. The method of claim 12, wherein the radial compression is prior to selecting the at least one wavelength.

14. The method of claim 13, wherein the target medium comprises a background medium and an object medium having different compressibility.

15. The method of claim 14, wherein radially compressing the target medium causes greater compression of the background medium than of the object medium, so that a ratio of object medium to background medium is increased.

16. A method of selecting an optimal wavelength of near infrared energy for imaging in a scattering target medium, comprising:
   providing a source for directing at least one wavelength of near infrared energy into the target medium;
   providing a detector for measuring diffusely scattered near infrared energy emerging from the target medium;
   directing a wavelength of near infrared energy into the target medium;
   measuring the emerging diffusely scattered near infrared energy from the target with at least one detector; and
   adjusting the wavelength of the near infrared energy based on the measured emerging diffusely scattered near infrared energy to maximize the total path length and maintain an acceptable energy density at a detector; and selecting at least one wavelength of near infrared energy having a maximized total path length through the target medium from the source to at least one detector;

providing a plurality of detectors at a plurality of distances from the source, and selecting a single wavelength to maximize the total path length of near infrared energy from the source to a detector furthest from the source and to maintain an acceptable energy density at the farthest detector.

17. The method of claim 16, wherein the wavelength is adjusted to increase the total path length and decrease the energy density at a detector.

18. The method of claim 16, wherein the wavelength is adjusted to decrease the total path length and increase the energy density at a detector.

19. A method for collecting data for use in image reconstruction of a scattering target medium, comprising:

providing a source for directing at least one wavelength of near infrared energy into a target medium wherein the at least one wavelength is selected to maximize the total path length of near infrared energy propagating through the target medium from the source to a detector and to maintain an acceptable energy density at the detector;

providing a detector for measuring diffusely scattered near infrared energy emerging from the target medium;

directing at least one selected wavelength of near infrared energy into the target medium; and measuring at least one wavelength of diffusely scattered near infrared energy emerging from the target medium;

providing a plurality of detectors at a plurality of distances from the source, and selecting a single wavelength to maximize the total path length of near infrared energy from the source to a detector furthest from the source and to maintain an acceptable energy density at the farthest detector.

20. A system for enhanced imaging of a scattering target medium, comprising:

means for selecting at least one wavelength of near infrared energy, wherein the at least one wavelength of near infrared energy is selected to maximize the total path length of near infrared energy propagating through the target medium from the source to a detector and to maintain an acceptable energy density at the detector;

a source for directing at least one wavelength of near infrared energy into a target medium; and a detector for measuring diffusely scattered near infrared energy emerging from the target medium;

a means for reconstructing an image of the properties of the target medium;

a plurality of detectors disposed at a plurality of distances from the source; and a means for selecting a wavelength to maximize the total path length of near infrared energy from the source to a detector farthest from the source and to maintain an acceptable energy density at the farthest detector.

21. A system for enhanced imaging of a scattering target medium, comprising:

a source for directing at least one wavelength of near infrared energy into a target medium wherein the at least one wavelength is selected to maximize the total path length of near infrared energy propagating through the target medium from the source to a detector and to maintain an acceptable energy density at the detector;

a detector for measuring diffusely scattered near infrared energy emerging from the target medium;

a means for reconstructing an image of the properties of the target medium;

a plurality of detectors disposed at a plurality of distances from the source; and a means for selecting a wavelength to maximize the total path length of near infrared energy from the source to a detector farthest from the source and to maintain an acceptable energy density at the farthest detector.

\* \* \* \* \*